United States Patent
Covey et al.

[11] Patent Number: 5,412,208
[45] Date of Patent: May 2, 1995

[54] ION SPRAY WITH INTERSECTING FLOW

[75] Inventors: Thomas R. Covey, Richmond Hill; Joseph F. Anacleto, Brampton, both of Canada

[73] Assignee: MDS Health Group Limited, Etobicoke, Canada

[21] Appl. No.: 181,529

[22] Filed: Jan. 13, 1994

[51] Int. Cl.$^6$ ............................................. H01J 49/10
[52] U.S. Cl. .................................... 250/288; 250/281; 250/282
[58] Field of Search ................... 250/288, 288 A, 281, 250/282

[56] References Cited

U.S. PATENT DOCUMENTS

4,861,988  8/1989  Henion et al. ............... 250/288
4,935,624  6/1990  Henion et al. ............... 250/288

Primary Examiner—Paul M. Dzierzynski
Assistant Examiner—Kiet T. Nguyen
Attorney, Agent, or Firm—Bereskin & Parr

[57] ABSTRACT

Liquid from a liquid chromatograph or other sample source, preferably assisted by a high velocity coaxial gas jet, is sprayed through a capillary tube producing a flow in a first direction of charged droplets. A flow of heated gas, in a second direction different from the first direction, intersects the droplet flow at a region upstream of an orifice. The flows mix turbulently, with the second flow helping to evaporate the droplets to produce ions and helping to move the evaporating droplets toward the orifice, providing a focusing effect. Ions are drawn through the orifice into a mass analyzer and analyzed. Alternatively the flows of liquid and heating gas can be directed toward each other and at right angles to the axis through the orifice, and the inhaling effect of the orifice can be used to draw droplets toward it, or a third gas flow can be used for this purpose. The heated intersecting gas flow typically provides an increase in sensitivity (ion counts per second) of between 10 and 100 times. Heating the droplet plume also allows controlled desaturation of ions and in increase in the number of charges on them, without degrading the ions.

35 Claims, 10 Drawing Sheets

ION SPRAY WITH INTERSECTING FLOW

FIELD OF THE INVENTION

This invention relates to method and apparatus for forming ions from a liquid and for directing such ions into a mass analyzer, typically a mass spectrometer.

BACKGROUND OF THE INVENTION

Electrospray interfaces are commonly used to receive liquid from a liquid sample source such as a liquid chromatograph ("LC") and to produce ions which are delivered to a mass spectrometer. In electrospray, liquid from the LC is directed through a free end of a capillary tube, the tube being connected to one pole of a high voltage source. The free end of the capillary tube is spaced from an orifice plate having an orifice leading (directly or through other equipment) into the mass analyzer vacuum chamber. The orifice plate is connected to the other pole of the high voltage source. The electric field generates a spray of charged droplets, producing liquid flow without a pump, and the droplets evaporate to produce ions.

Because electrospray can handle only a very small flow (larger flows produce larger droplets, causing the ion signal to fall off and become unstable), a new technique was developed, which can be referred to as nebulizer gas spray. The nebulizer gas spray technique, shown in U.S. Pat. No. 4,861,988 issued Aug. 29, 1989 to Cornell Research Foundation, involves providing a cocurrent flow of high velocity nebulizer gas coaxial with the capillary tube. The nebulizer gas nebulizes the liquid to produce a mist of droplets which are charged by the applied electrical field. While electrospray functions poorly at liquid flows over about 10 microliters per minute, nebulizer gas spray functions reasonably well at liquid flows of up to between 100 and 200 microliters per minute. However even with nebulizer gas spray, it is found that with liquid flows of the order of about 100 microliters per minute, the sensitivity of the instrument is less than at lower flows, and that the sensitivity reduces substantially at liquid flows above about 100 microliters per minute. It is believed that at least part of the problem is that at higher liquid flows, larger droplets are produced and do not evaporate to release ions before these droplets reach the orifice. Therefore, much sample is lost.

Various attempts have been made to improve the sensitivity of instruments using nebulizer gas spray and electrospray. For example, as shown in U.S. Pat. No. 4,935,624 issued Jun. 19, 1990, attempts have been made to heat the liquid before it is sprayed through the capillary tube. However because heating the liquid in the capillary tube to a high temperature will degrade thermally labile analytes, this method is not desirable and has produced only a limited increase in sensitivity.

In another attempt to improve the results when using electrospray, two researchers at the University of Alberta in Alberta, Canada, namely Paul Kebarle and Michael Ikonomou, have recently suggested surrounding an electrospray capillary with a cocurrent coaxial sheath of heated entraining gas. The flow used is not a nebulizing flow, but rather is a laminar flow of heating gas. It is found that this can increase the sensitivity of the instrument by 3 to 5 times, but in practice the device has proven temperamental and the improvement is available only within a very narrow range of operating parameters.

SUMMARY OF THE INVENTION

It is therefore an object of the present invention to provide a liquid analyte spray apparatus and method in which an intersecting flow of heated gas is used to provide improved sensitivity. In one aspect the invention provides a method of analyzing ions from trace sample molecules in a liquid, comprising:
(a) providing a chamber having a capillary tube therein, said capillary tube having a free end, said chamber having an orifice member spaced from said free end and having an orifice therein,
(b) directing said liquid through said capillary tube and out said free end,
(c) generating an electric field in said chamber between said free end and said orifice member,
(d) producing from said free end a first flow, of charged droplets of said liquid, and directing said first flow in a first direction,
(e) producing a second flow, of gas, and heating said second flow,
(f) directing said second flow in a second direction different from said first direction for said second flow to intersect said first flow at a selected region for turbulent mixing of said first and second flows in said region,
(g) the heated gas from said second flow acting to assist evaporation of droplets in said first flow to release ions therefrom,
(h) and drawing ions produced from said droplets through said orifice into an analyzer located outside said chamber beyond said orifice member.

In another aspect the invention provides apparatus for analyzing ions from trace sample molecules in a liquid comprising:

(a) a chamber, (b) a capillary tube to receive said liquid and having a first free end in said chamber for discharging said liquid into said chamber, (c) an orifice member in said chamber having an orifice therein and being spaced from said free end, said orifice defining an outlet from said chamber, (d) means for creating an electric field between said free end and said orifice member (e) means for producing from said free end a first flow, of charged droplets of said liquid, and for directing said first flow in a first direction, (f) means for producing a second flow of gas in said chamber, and means for heating said second flow, (g) means for directing said second flow in a second direction different from said first direction for said second flow to intersect said first flow at a selected region for turbulent mixing of said first and second flows at said region, (h) the heated gas from said second flow acting to assist evaporation of droplets in said first flow to release ions therefrom, (i) and means for drawing ions produced from said droplets through said orifice into an analyzer located outside said chamber beyond said orifice member.

Further objects and advantages of the invention will appear from the following description, taken together with the accompanying drawings.

BRIEF DESCRIPTION OF THE DRAWINGS

In the accompanying drawings:

FIG. 1 is a diagrammatic view of prior art ion spray apparatus;

DETAILED DESCRIPTION OF PREFERRED EMBODIMENTS

Figure 1:
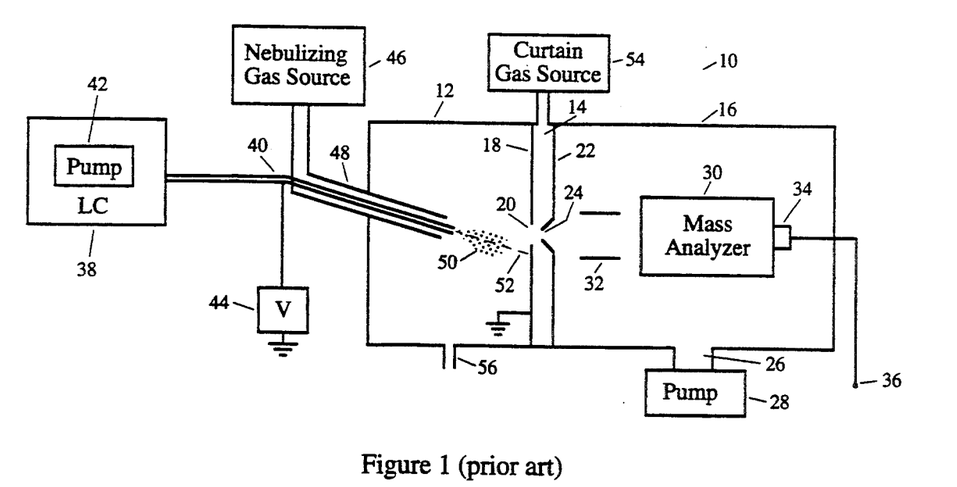

Reference is first made to FIG. 1 which shows diagrammatically a prior art nebulizer gas spray analyzer 10 generally as shown in U.S. Pat. No. 4,861,988. The analyzer 10 includes an atmospheric pressure ionization chamber 12, a gas curtain chamber 14, and a vacuum chamber 16. The ionization chamber 12 is separated from the gas curtain chamber 14 by an orifice plate 18 containing an inlet orifice 20. The gas curtain chamber 14 is separated from the vacuum chamber 16 by an outlet plate 22 containing an orifice 24.

The vacuum chamber 16, which is evacuated through outlet 26 by pump 28, contains a commercially available mass analyzer 30 (typically a tandem triple quadrupole mass spectrometer). Ions from ionization chamber 12 and drawn through orifices 20, 24 are focused by ion lens elements 32 into analyzer 30. A detector 34 at the end of the analyzer 30 detects ions which pass through the analyzer and supplies a signal at terminal 36 indicative of the number of ions per second which are detected.

The liquid sample to be analyzed is typically supplied from a liquid chromatograph 38 through capillary tube 40 into chamber 12. The flow rate of the liquid through capillary tube 40 is determined by the LC pump 42. The portion of capillary tube 40 which enters chamber 12 is made of a conductive material and has one pole (depending on the polarity of the ions desired) of a voltage source 44 connected to it. The other pole of source 44, and plate 18, are grounded. A source 46 of pressurized gas (e.g. nitrogen) supplies a sheath tube 48 coaxial with and encircling capillary 40 with a high velocity nebulizing gas flow which nebulizes fluid ejected from capillary 40. The mist of droplets 50 formed is carried toward the orifice 20 by the nebulizing flow. The droplets 50 are charged by the voltage applied to capillary 40, and as the droplets evaporate, ions are released from them and are drawn toward and through the orifices 20, 24.

As is conventional, the axis 52 of capillary 40 is aimed slightly off axis, i.e. slightly below the orifice 20. Thus, large droplets which do not fully evaporate by the time they reach orifice 20 simply impact against the plate 18 and run down the plate where they are collected (by means not shown). Ions released from the fine droplets which have evaporated are drawn through the orifices 20, 24 into the vacuum chamber 16, where they are focused into the analyzer 30. As is well known, a curtain gas (typically nitrogen) from curtain gas source 54 diffuses gently out through orifice 20 to prevent contaminants in chamber 12 from entering the vacuum chamber 16. Excess gas leaves chamber 12 via outlet 56.

As mentioned, a difficulty with the apparatus shown in FIG. 1 is that as the liquid flow rate is increased, the sensitivity of the instrument does not increase proportionately. It is believed that this is because much of the increased sample flow is lost in coarser droplets which do not have time to evaporate by the time they reach interface plate 18. Increasing the velocity of the nebulizing gas flow through sheath tube 48 provides only very limited improvement.

Figure 2:
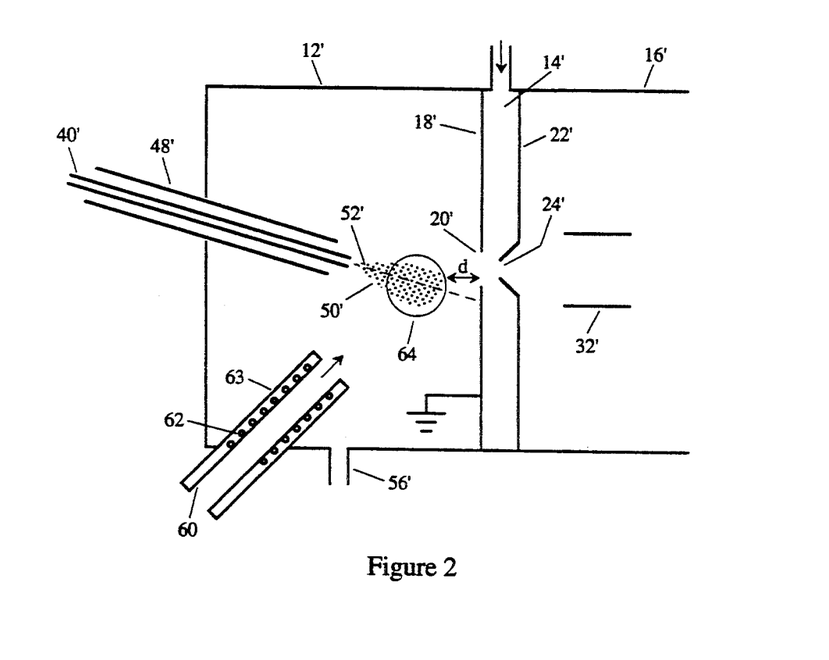
FIG. 2 is a diagrammatic view of apparatus according to the invention and showing intersecting flows of gas.

Reference is next made to FIG. 2, which shows a portion of the FIG. 1 apparatus fitted with an improvement according to the invention. In FIG. 2 primed reference numerals indicate parts corresponding to those of FIG. 1.

The difference between the FIG. 1 and FIG. 2 apparatus is that in FIG. 2, a flow of intersecting heated gas (typically nitrogen but clean dry air can be used) is provided via tube 60. The diameter of tube 60 may vary, but in one embodiment the internal diameter of tube 60 was 6.0 mm. The area of the tube 60 (28.3 mm$^2$) was much larger than the area of the annulus between nebulizing gas tube 48' and capillary tube 40'. (The inner diameter of tube 48' was 0.432 mm, and the outer diameter of capillary tube 40' was 0.4 mm, so the area of the annulus between them was only 0.021 mm$^2$.)

The flow of gas through tube 60 is relatively high. For example, while the flow of nebulizing gas through tube 48' is typically one liter per minute, the flow of gas through tube 60 may be of the order of 1 to 10 liters per minute. The gas in tube 60 is heated by heating coil 62 which encircles tube 60. Insulation 63 encircles heater coil 62 and the downstream part of tube 60 which is not encircled by the heater coil, to minimize heat loss from the gas before it leaves the tube 60.

The velocity of the nebulizing gas from tube 48' is normally very high, typically about 100 to 1,000 meters per second (the sonic limit) and a flow rate in the range 0.25 to 2.0 liters per minute as it leaves tube 48'. Of course this velocity is reduced downstream of the free end of tube 48' due to mixing with the surrounding gas and with the liquid. The velocity of the gas from tube 60 is much lower and varies (depending on flow) from about 0.25 to 10 meters per second and a flow rate in the range 0.25 to 10 liters per minute.

The flow of gas from tube 60 is preferably aimed to intersect the flow of gas and droplets from tubes 40', 48' at region 64, outlined by a circle. The downstream edge of region 64 is spaced slightly in front of the orifice 20'. Preferably such spacing, indicated by dimension d, is about 1 centimeter. It is found that spacing the intersection region 64 upstream of orifice 20' helps reduce the likelihood of large droplets entering the orifice 20' and therefore reduces chemical noise in the signal detected at detector 34.

The flow of heated gas from tube 60, as it intersects the flow of gas and droplets from tubes 40', 48', produces turbulent mixing in front of the orifice 20'. The turbulent mixing with heated gas serves to rapidly evaporate the droplets 50', thus increasing ion emission and reducing sample wastage. Without the turbulent mixing from the heated cross flow of gas, large droplets are observed to impinge on plate 18' before ion emission can occur, resulting in considerable sample wastage. With the heated cross flow all or most of the population of droplets is reduced to sufficiently small dimensions (<1 micron for each droplet) for ion emission to occur. In addition, the force of the jet of gas from tube 60 has a focusing effect, pushing the mist of fine droplets 50' toward the orifice 20' so that ion emission can occur in a region immediately in front of the orifice and a greater flux of ions can then pass through the orifice into the ion focusing element 32'. As will be seen, both the heating and focusing effects are useful, and they appear to function together to produce very substantial improvements in sensitivity.

Figure 3A:
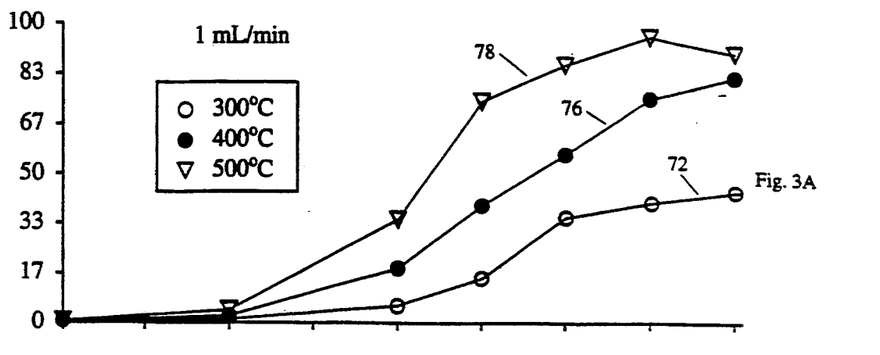
FIG. 3A, 3B, and 3C are graphs showing variation of sensitivity with intersecting gas flow and temperature for liquid flows of 1 milliliter per minute, 200 microliters per minute, and 50 microliters per minute respectively.
Figure 3B:
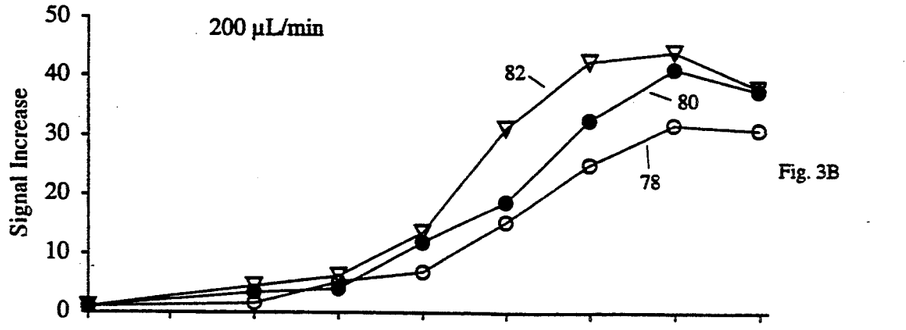
Figure 3C:
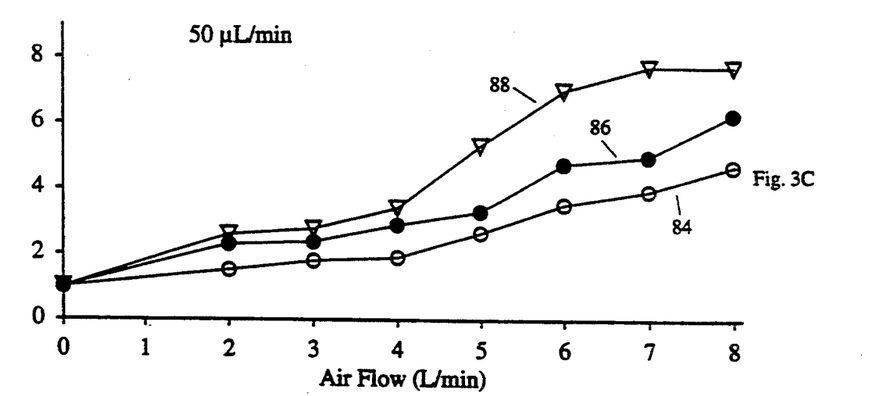

While the method and apparatus shown in connection with FIG. 2 improves sensitivity over a wide range of liquid flow rates, it is found that the sensitivity increases are greater at high liquid flow rates. For purposes of this description, it is noted that liquid flow rates from an LC may be classified as follows:

1. 1 to 25 microliters per minute—low flow
2. 25 to 75 microliters per minute—low to intermediate flow
3. 75 to 300 microliters per minute—high intermediate flow
4. 300 to 2,000 microliters per minute (and above)—high flow Reference is next made to FIGS. 3A to 3C, which show sensitivity improvements achieved at high, high intermediate and low intermediate liquid flow rates respectively, utilizing the device shown in FIG. 2.

Specifically, FIGS. 3A to 3C are graphs showing on the horizontal axis gas flow through tube 60 in liters per minute. On the vertical axis the relative signal increase for the compound being analyzed is displayed. To obtain this value the signal in ion counts per second (cps), at any experimental point in the curve, is normalized to the signal obtained when no intersecting gas flow from tube 60 is used. Thus the first value (at air flow=0) for relative signal increase on all curves in FIGS. 3A to 3C is 1. In each graph of FIGS. 3A to 3C, three curves are shown for heater temperatures of 300° C., 400° C., 500° C. and respectively It is noted that these temperatures were measured at the wall of tube 60 directly beneath the heater coils 62 and that the temperature of the gas leaving tube 60 would be substantially lower, and would be between about 40% and 50% of the heater temperature.

The compound used to produce the graphs of FIGS. 3A to 3C was omeprazole, dissolved in a solution which was about 65% water. For each of FIGS. 3A, 3B, and 3C, 50, 5, and 0.25 picograms of omeprazole respectively were injected onto a commercially available high pressure liquid chromatograph column (HPLC) of 10 cm length. The omeprazole then eluted from the column and passed into chamber 12 to produce each measured point on the curves. The signal is obtained by filtering the parent molecular ion at m/z 346 through the first mass analyzer of a triple quadrupole mass spectrometer, and then after fragmentation in the collision cell region, measuring the signal obtained on the most intense daughter ion at m/z 198 of omeprazole. For FIG. 3A the column internal diameter was 4.6 mm thus accommodating a liquid flow of 1 milliliter per minute. For FIG. 3B the column internal diameter was 2.1 mm, thus accommodating a liquid flow of 200 microliters per minute. For FIG. 3C the column internal diameter was 1 mm, thus accommodating a liquid flow of 50 microliters per minute.

In FIG. 3A, where the liquid flow rate was 1 milliliter per minute (high flow rate), curves 72, 76, 78 were produced at heater temperatures of 300° C., 400° C. and 500° C. respectively. As mentioned, with no gas flow through tube 60, the relative signal increase is 1, i.e. no signal increase. The signal increased approximately 5 times at a gas flow of 4 liters per minute with the heater at 300° C. (curve 72), and increased by 50 times at the same gas flow rate when the heater was 500° C. (curve 78). As the gas flow rate then increased to 7 liters per minute, the relative signal increase rose to 100 times at a heater temperature of 500° C. (curve 78). The sensitivity increase was somewhat less but still substantial at lower heater temperatures, as shown.

It is believed that some of the reasons why there was limited sensitivity increase up to 4.0 liters per minute gas flow through tube 60 in FIG. 3A, were that at lower gas flow rates the focusing effect of the intersecting flow was less pronounced, and also the total quantity of heat added to the intersection region 64 was reduced since less heated gas was delivered to this region.

Reference is next made to FIG. 3B, which shows curves 78, 80, 82 similar to those of FIG. 3A but with a liquid flow rate of 200 microliters per minute (high intermediate flow), and using heater temperatures of 300° C., 400° C. and 500° C. respectively.

With no gas flow through tube 60, the relative signal increase in FIG. 3B is 1, i.e. no signal increase. At a gas flow rate from tube 60 of 7 liters per minute, with the heater 62 at 500° C. (curve 82), the ion signal was increased by more than 40 times.

Reference is next made to FIG. 3C, which shows ion signals achieved at a liquid flow rate of 50 microliters per minute (low to intermediate flow). Curves 84, 86, 88 represent ion signals achieved at various gas flow rates from tube 60 at heater temperatures of 300° C., 400° C. and 500° C. respectively.

In FIG. 3C it will be seen that, without any gas flowing through tube 60, the relative signal increase is 1, i.e. no signal increase. With a gas flow through tube 60 of about 7 liters per minute and at the highest temperature used (500° C. for the heater 62), the relative signal increase is approximately 8 times (curve 88).

Since the problem of a decrease in sensitivity for nebulizer gas spray occurs primarily at higher liquid flows, and since it is usually desired to operate instruments at higher flows for greater throughput, the very large increases in sensitivity at high liquid flows are well matched to practical needs.

Figure 4A:
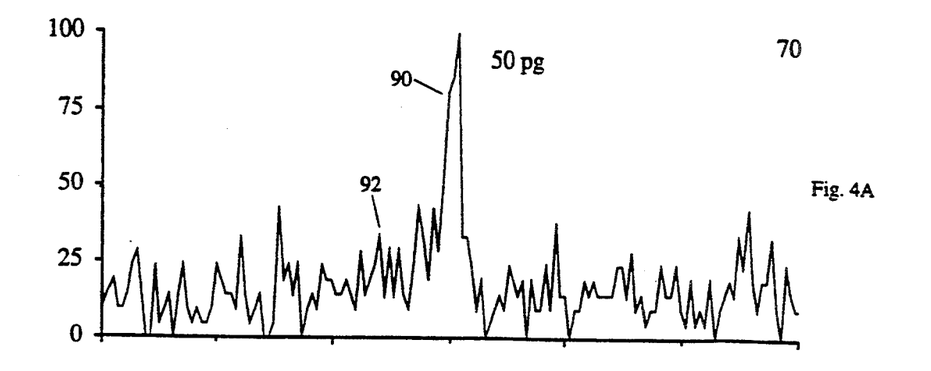
FIGS. 4A, 4B and 4C are chromatograms for liquid flow of 1 milliliter per minute.
Figure 4B:
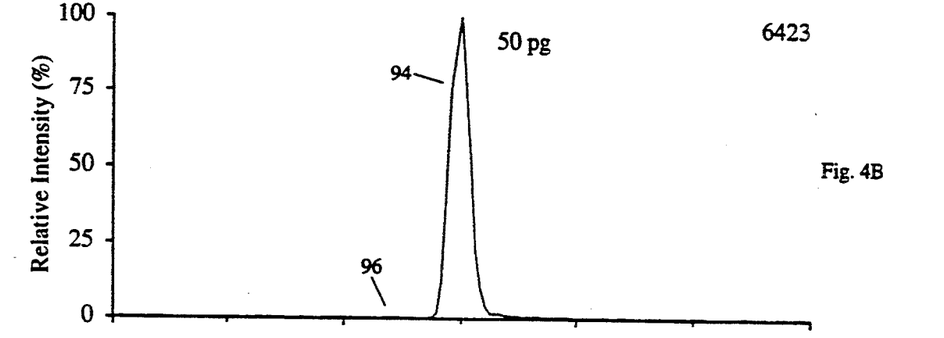
Figure 4C:
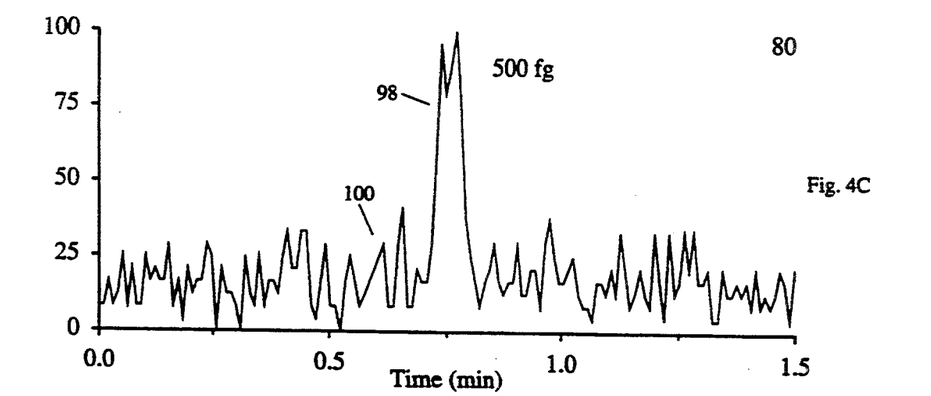

Reference is next made to FIGS. 4A to 4C inclusive, which show ion current chromatograms for omeprazole injected onto a 4.6 mm I.D. HPLC column at 1 milliliter per minute (high flow) then eluting into chamber 12' through capillary 40' after approximately 0.75 minutes. The mobile phase was composed of approximately 65% water. In the example shown in FIGS. 4A and 4B 50 picograms of analyte was injected. In the example shown in FIGS. 4C, 0.5 picograms (500 femtograms) was injected.

In FIGS. 4A to 4C, the vertical scale is normalized and is indicated as relative intensity, with the highest peak representing 100%. The number of counts per second represented by the peak is shown in the upper right hand corner of each drawing. The signal is obtained by filtering the parent molecular ion at m/z 346 through the first mass analyzer of a triple quadrupole mass spectrometer, and then after fragmentation in the collision cell region, measuring the signal obtained on the most intense daughter ion at m/z 198 of omeprazole. Time in minutes is plotted on the horizontal scale.

In FIG. 4A, where 50 picograms of omeprazole were injected, with no gas flow through tube 60, it will be seen that the peak 90 representing omeprazole was 70 cps, and that there was a significant amount of background noise, represented at 92. Since it is generally considered that the limit of reliable detection requires the signal to be about twice the level of the background noise, the system and method represented by FIG. 4A were near the limit of detection with 50 picograms of analyte.

The chromatogram shown in FIG. 4B was made under the same conditions as for FIG. 4A, with 50 picograms injected, the only difference being that a flow of 7 liters per minute of heated gas was injected through tube 60, with the heater 62 operated at 500° C. It will be seen that the omeprazole peak 94 was 6,423 cps, more than a ninety-fold increase. The background noise 96 remained nearly unchanged in absolute amplitude from that shown in FIG. 4A and is therefore virtually unnoticeable in FIG. 4B.

In FIG. 4C, as mentioned, the same liquid and intersecting gas flow rates and gas temperature were used as in FIG. 4B, but only 0.5 picograms of analyte were injected, 100 fold less than in FIGS. 4A and 4B. It will be seen that the peak 98 representing omeprazole was now 80 cps, i.e. slightly more than that of FIG. 4A, although only 1% of the amount of sample was used. The background noise 100 was slightly less for FIG. 4C than for FIG. 4A. Thus, the sensitivity achieved in the FIG. 4C experiment was more than 100 times greater than that achieved for FIG. 4A.

Figure 5A:
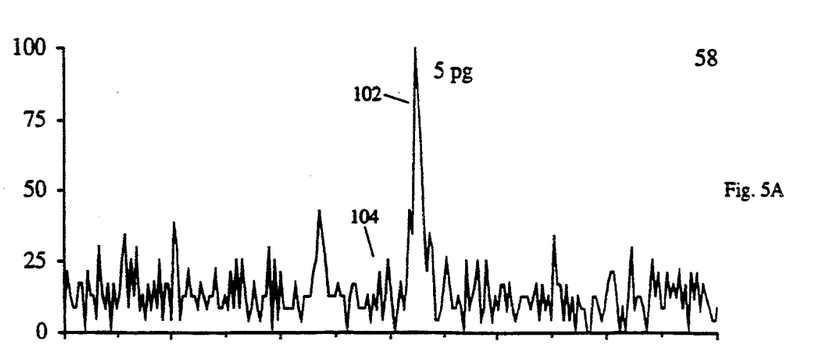
FIGS. 5A, 5B, and 5C are chromatograms for liquid flows of 200 microliters per minute.
Figure 5B:
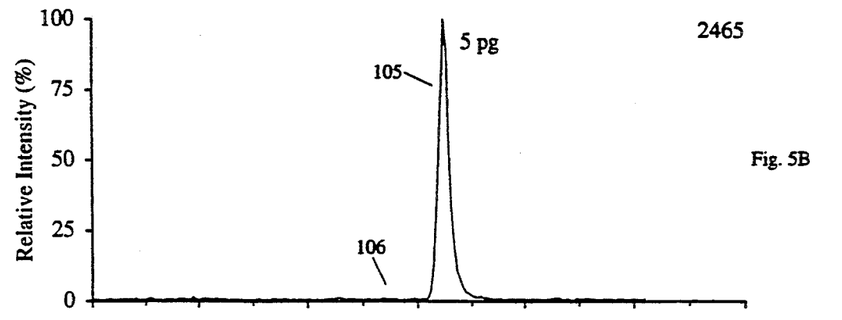
Figure 5C:
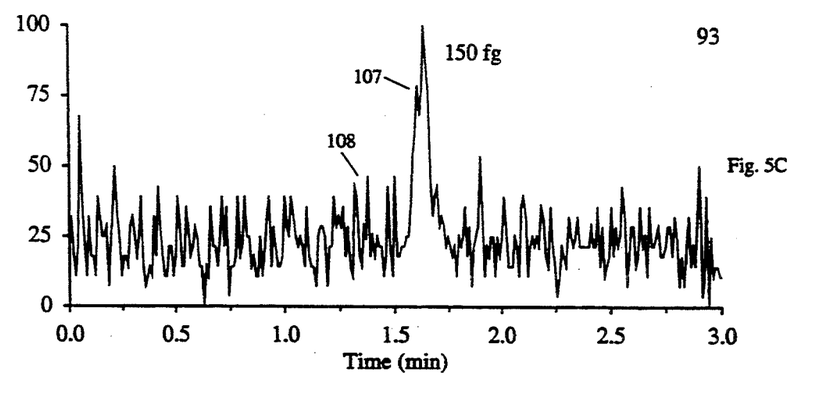

Reference is next made to FIGS. 5A to 5C inclusive, which show ion current chromatograms for omeprazole injected onto a 2.1 mm I.D. HPLC column at 200 microliter per minute (high intermediate flow) then eluting into chamber 12' through capillary 40' after approximately 1.6 minutes. The mobile phase was composed of approximately 65% water. In the example shown in FIGS. 5A and 5B 5 picograms of analyte was injected. In the example shown in FIGS. 5C 0.15 picograms (150 femtograms) was injected.

In FIG. 5A no gas was injected through tube 60. The peak 102 representing omeprazole was 58 cps, with significant background noise 104.

For FIG. 5B the same test procedure and parameters as for FIG. 5A were used, except 7L/min. of nitrogen at 500° C. was injected through tube 60. The peak 105 was 2465 cps, with no significant increase in background noise 106. The sensitivity achieved in the experiment shown in FIG. 5B was more than forty times that achieved in FIG. 5A. In FIG. 5C the same experimental conditions were used as for FIG. 5B except 0.15 picograms was injected. The cps for the peak 107 were 93, i.e. slightly greater than those for the peak 102 in FIG. 5A even though 33 times less sample was injected.

Figure 6A:
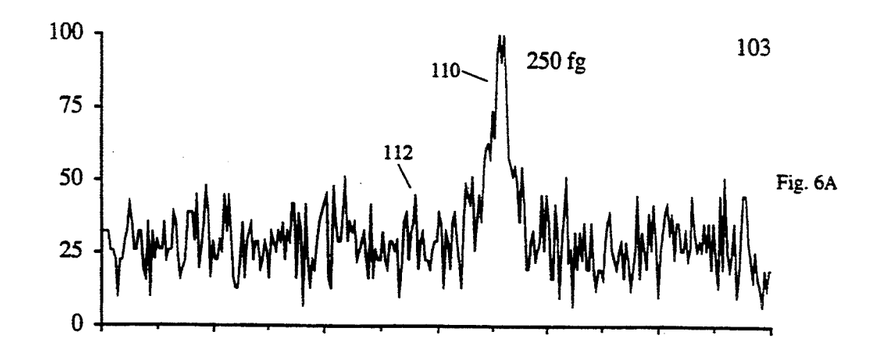
FIGS. 6A, 6B, and 6C are chromatograms for liquid flows of 50 microliters per minute.
Figure 6B:
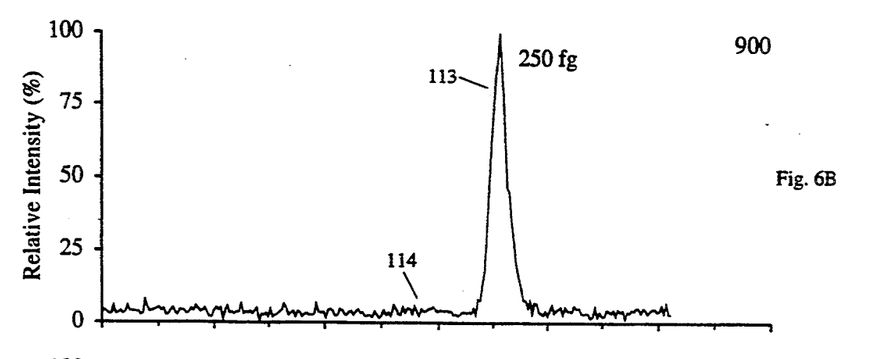
Figure 6C:
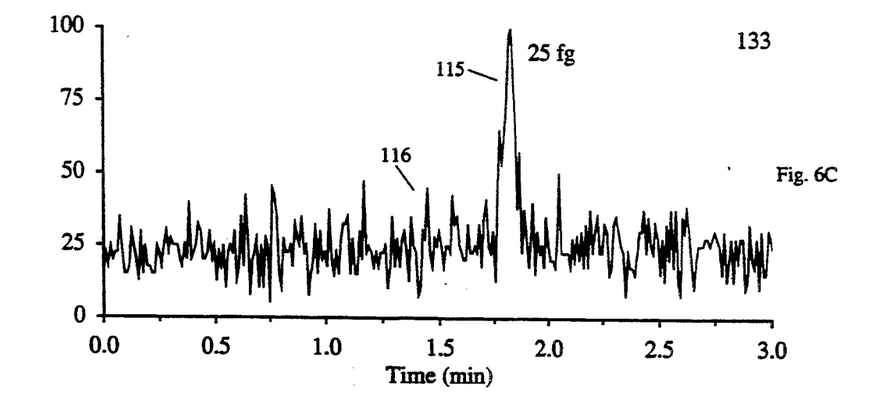

Reference is next made to FIGS. 6A to 6C inclusive, which show ion current chromatograms for omeprazole injected onto a 1.0 mm I.D. HPLC column at 50 microliter per minute (low to intermediate flow) then eluting into chamber 12' through capillary 40' after approximately 1.8 minutes. The mobile phase was composed of approximately 65% water. In the example shown in FIGS. 6A and 6B 250 femtograms of analyte was injected. In the example shown in FIGS. 6C 25 femtograms was injected.

In FIG. 6A no gas was injected through tube 60. The peak 110 representing omeprazole was 103 cps and there was significant background noise 112.

In FIG. 6B, 7 liters per minute of gas were injected through tube 60 with the heater 60 at 500° C. The same total analyte quantity was injected as in 6A (250 femtograms). The peak 113 representing omeprazole was 900 counts per second, with background noise 114 about the same as in FIG. 6A. Thus, even at this relatively low flow rate, the sensitivity was increased by about nine times. In FIG. 6C the same experimental conditions were used as for FIG. 6B except 25 picograms was injected. The cps for the peak 117 were slightly greater than those for the peak 110 in FIG. 6A even though 10 times less sample was injected.

Figure 7A:
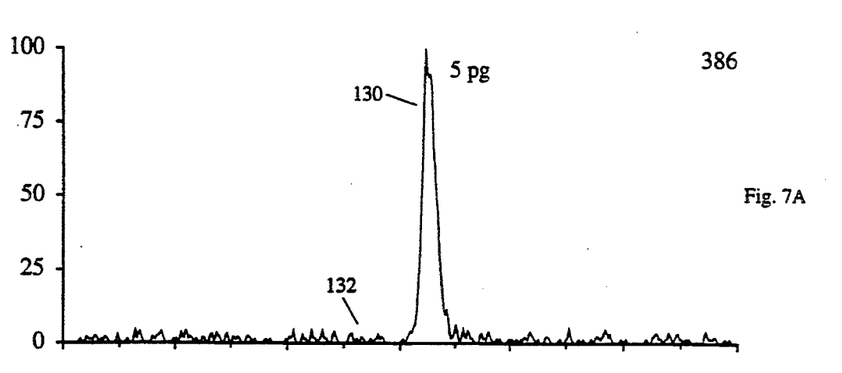
FIGS. 7A, 7B, and 7C are chromatograms for liquid flows of 200 microliters per minute.
Figure 7B:
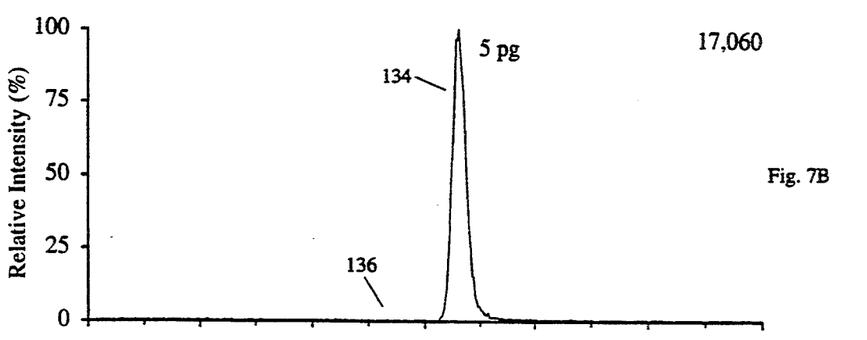
Figure 7C:
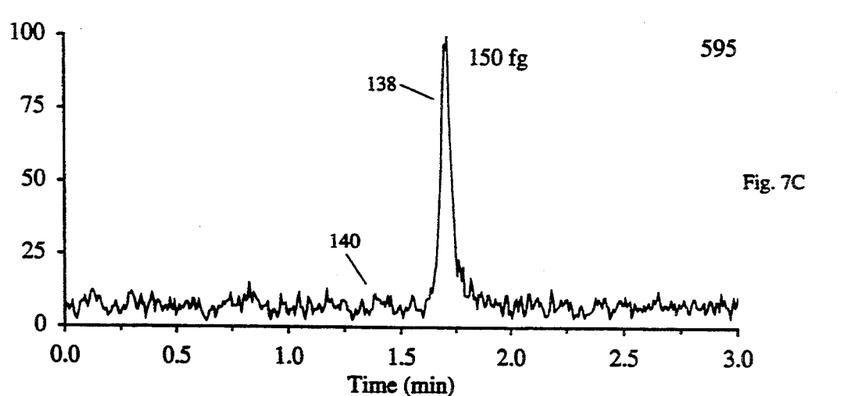

Reference is next made to FIGS. 7A to 7C inclusive, which show chromatograms for another compound, ritodrine, injected through capillary 40' at a flow rate of 200 microliters per minute onto a 2.1 mm ID HPLC column with the mobile phase solution containing about 35% water. In FIG. 7A 5 picograms of analyte was injected. No gas was injected through tube 60. This produced peak 130 at 386 cps with low background noise 132.

FIG. 7B was made using the same method and parameters as in FIG. 7A, except that 7 liters per minute of heated gas, with the heater 62 adjusted to 400° C., was injected though tube 60. This produced a peak 134 at 7,060 cps (a 44 times increase in sensitivity), with insignificant background noise 136.

FIG. 7C was made by injecting 150 femtograms of ritodrine through capillary 40', again at 200 microliters per minute. The same heated gas flow rate and temperature were used as in FIG. 10B. This produced peak 138 at 595 cps, with relatively low background noise 140. The sensitivity was nearly the same as in FIG. 7A even though 33 times less material was injected.

Figure 8A:
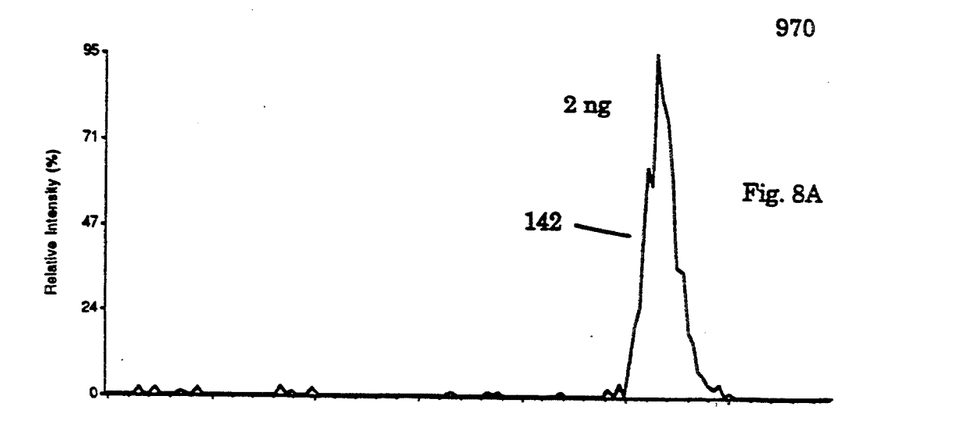
FIGS. 8A and 8B are chromatograms for liquid flows of 2000 microliters per minute.
Figure 8B:
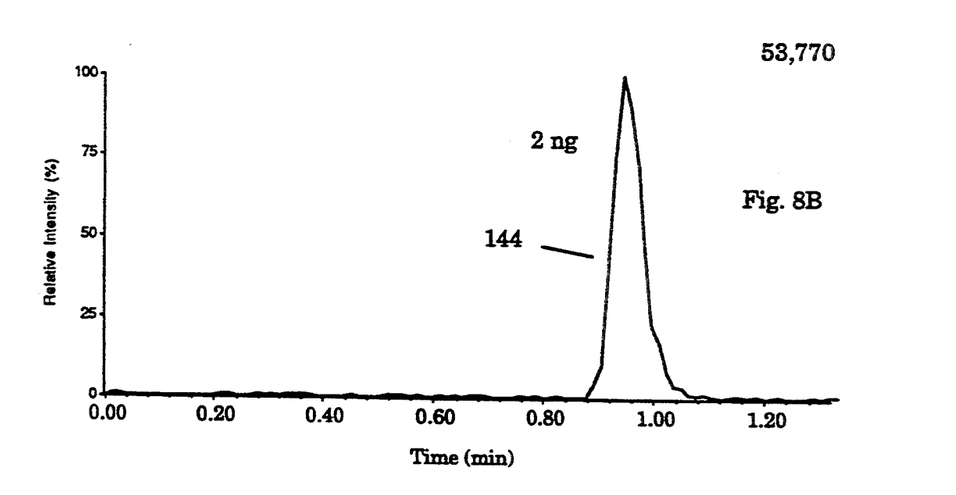

All the above graphs were produced using positive ions. FIGS. 8A and 8B show chromatograms produced using negative ions. In FIGS. 8A and 8B, 2 nanograms of taurochloric acid [0.4 pg/μL] was injected onto a 4.6 mm ID HPLC column at a flow rate of 2 milliliters per minute (high flow rate) using a mobile phase solution of 40% water. In FIG. 8A no gas was injected through tube 60, while in FIG. 8B gas at 7 liters per minute, with heater 62 at 500° C., was injected. This produced a peak 142 in FIG. 8A of 970 cps, and a peak 144 in FIG. 8B of 53,770 cps, a 55 times increase.

While FIGS. 8A, 8B show injected liquid flows of 2 milliliters per minute, higher flows, e.g. 3 milliliters per minute, may also be used with the invention, with a resultant sensitivity increase.

Three unexpected effects obtained with the present invention were: a) a large sensitivity increase as described above, b) a general lack of thermal degradation of labile compounds despite the substantial amount of heat applied, and c) the ability to use the injected heat to carefully regulate the degree to which a protein molecule can be denatured. These three effects will be further described below.

All three example compounds described above, omeprazole, ritodrine, and taurocholic acid are materials that normally degrade when exposed to temperatures in excess of 100° C., yet signal from the intact molecular ion increased rather than decreased when exposed to gases at temperatures in great excess of this.

Figure 9A:
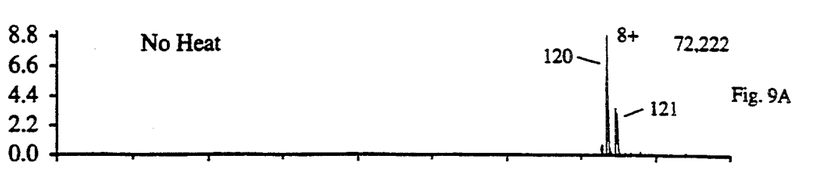
FIGS. 9A to 9F inclusive are graphs showing mass spectra at liquid flows of 5 microliters per minute.
Figure 9B:
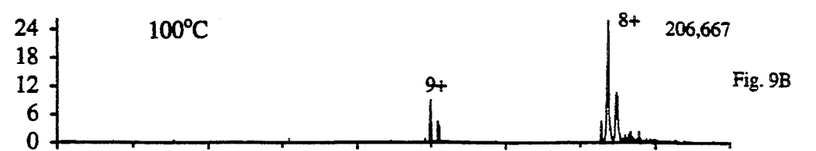
Figure 9C:
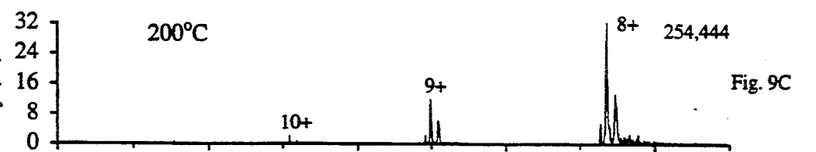
Figure 9D:
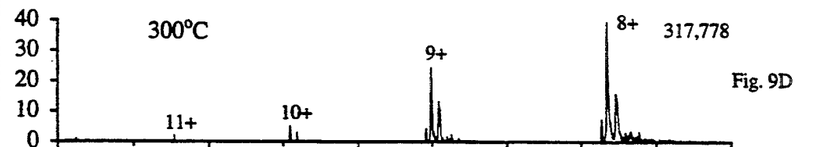
Figure 9E:
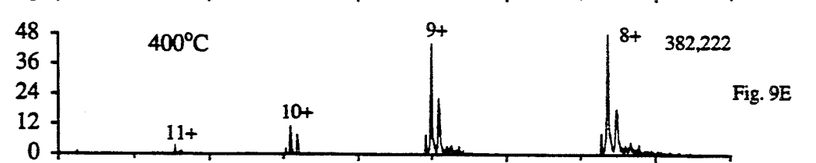

Protein molecules, which have very high molecular weights and are even more labile than the above mentioned compounds, were also tested. Reference is made to FIGS. 9A to 9F inclusive which show the mass spectra of the protein wheat germ agglutinin (molecular weight=17,081) when taken with varying levels of heat and gas flow through tube 60. On the horizontal axis is plotted the mass-to-charge ratio of the ions being generated. The total signal as measured in counts per second is in the upper right hand corner of each spectrum. The vertical axis is normalized intensity relative to the most intense signal in the spectrum in FIG. 9F. In each case the sample, at a concentration of 1 milligram/milliliter, was dissolved in 100% water+1% formic acid and flowed through capillary 40' at a rate of 5 $\mu$L/min (low flow). In FIG. 9A there is no gas flow through tube 60. In FIGS. 9B to 9F the gas flow is 7 liters per minute at heater temperatures of 100° C., 200° C., 300° C., 400° C., and 500° C. respectively. Each peak in the spectra represent a multiply charged molecular ion. The number of charges on the ion associated with each peak is indicated by a number above the peak followed by a +sign, e.g. 8 positive charges for peak 121. The three effects described above are observed, namely: increase in sensitivity, freedom from thermal degradation, and protein denaturation resulting in the unfolding of the protein with increase in the number of charges observed on the molecule.

Figure 9F:
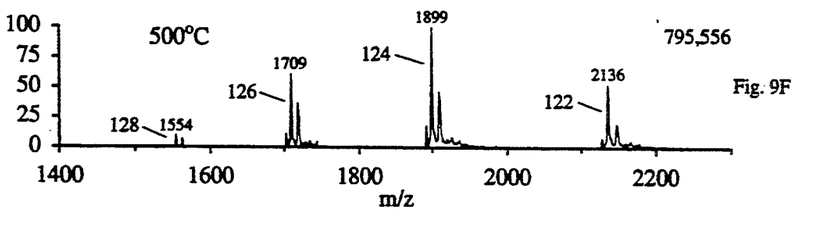

It will be seen that as the heater temperature 62 increases, the number of counts per second for the dominant peak increases from 72,222 in FIG. 9A to 795,556 in FIG. 9F (a ten fold increase in sensitivity at low flows). Also, more intact molecular ions appear with increasing charge state but no fragment ions from thermal degradation are observed. At least five other minor related proteins are also present in the sample (eg. peak 121 in FIG. 9A) and are observed as small satellite peaks around the major charge state ions. These are not fragments but rather different protein molecules present in this impure preparation of wheat germ agglutinin.

It is believed that thermal degradation does not occur for the following reason. The sample is transferred to the ion source in a flowing stream of liquid contained in a capillary transfer line. The liquid in the capillary is itself not heated. Even the tip of the nebulizer gas spray devise remains cool as a result of the adiabatic expansion of nebulizer gas. The heat is applied after the sprayer by a separate heated gas stream emanating from tube 60 which intersects the flow of liquid droplets. When the heated gas from tube 60 is applied to the droplets, the temperature of the droplets does not increase to a point where thermal degradation would occur; instead, the droplets begin to evaporate and cool at a rate nearly matching the thermal input from the heated gas. As the droplet dimensions become submicron, individual sample ions, clustered with a protective shell of a few solvent molecules, leave the droplet by the well known ion evaporation process, before the droplet becomes a solid residue. The ion-solvent cluster is rapidly drawn by applied voltage potentials out of the hot gas and into the cooler curtain gas where the final declustering of the ion from the solvent molecules occurs as a result of collisions with curtain gas molecules. The expansion into the vacuum chamber 16' provides further cooling. The residence time of the ion-solvent cluster species in the hot gas is a few milliseconds or less which limits the time for severe thermal degradative processes to occur. By severe degradative processes we refer to the fracturing of covalent chemical bonds in a molecule.

In FIGS. 9A to 9F, as the temperature is increased the number of charges on the molecular ions also increases. This is a result of the dissociation of hydrogen bonds and bonds held by Van Der Walls forces at the slightly elevated temperatures the molecules experience inside the evaporating droplets, causing the molecules (which are normally folded) to unfold. When the molecule unfolds, basic residues previously buried within the molecule, sequentially become exposed to solution protons and attract an additional charge. With this invention this process can be controlled and different degrees of denaturation are accessible by varying the temperature of gas from tube 60. This is illustrated in FIGS. 9A to 9F. With knowledge of the heat input one can make calculations regarding the bonding energies and stabilities of the different tertiary structures. The study of the non-covalent interactions of proteins with other molecules such as enzyme substrates, receptor ligands, and antibody antigens can be advanced in this way.

Although it is well known that heating causes denaturation, it had always been believed that such denaturation is a relatively slow process, taking between tens of seconds and minutes to occur. With this invention the denaturation effect is instantaneous. The moment the gas temperature is changed, the spectra are altered. The method and apparatus described will denature proteins more than one thousand times faster than processes known to occur in solution. This is an unexpected result. Since the lifetime of the droplets is known to be only a few milliseconds (e.g. less than 10 milliseconds), and since the method heats only the highly charged droplets, it follows that denaturation is occurring in a very short time, on the order of between microseconds and milliseconds. This capability would allow for very rapid determinations on large numbers of different tertiary conformations while consuming a very small amount of sample.

Additionally the denaturation facilitates analysis of many proteins by effectively extending the mass range of the mass spectrometer. Proteins that normally pick up only a few charges due to high degrees of folding could have a maximum mass charge ratio beyond the mass range of the mass analyzer. With this method described, more charges can be imparted to a molecule thus bringing the signal into the normal scanning range of the mass analyzer.

This effect was seen in FIGS. 9A to 9F for wheat germ agglutinin determined on a mass analyzer whose scanning limit was 2400 mass to charge units. The same effect was observed for other tightly folded proteins. Reference is made to FIG. 9A. In FIG. 9A, where there was no gas flow through tube 60, a single dominant peak 120 was obtained, of intensity 72,222 cps. Because only a single large peak was located and because the number of charges associated with the peak was not known, it was not possible reliably to determine the molecular weight of the substance being analyzed.

However, as shown in FIG. 9F, when heat is applied several consecutive charge states appear shown as the four peaks or groups of peaks 122, 124, 126, 128. With more than one charge state ion in the spectrum one can calculate the number of charges on each ion and thus obtain the molecular weight with the use of two simultaneous equations. In this case 8 positive charges were determined for peak 122, 9 for peak 124, 10 for peak 126 and 11 for peak 128. The mass to charge ratio for each peak 122 to 128 is shown above the peaks. This allowed the molecular weight of wheat germ agglutinin to be determined as 17,081.

It is found that the precise angle at which tube 60 is aimed is not highly critical and that variations can be made in this angle. However reference is made to FIG. 10, which shows at 52' the axis or trajectory of flow from tubes 40', 48', and shows at 150 the axis or trajectory of flow from tube 60. It will be seen that trajectory 52' can be resolved into a velocity component 52a which is parallel to the axis 152 of flow through the orifice 20', and a component 52b which is perpendicular to axis 152. Similarly, trajectory 150 can be resolved into a component 150a parallel to axis 152 and a component 150b perpendicular to axis 152. It is desirable that the flow of gas from tube 60 have some velocity component parallel to the axis 152 in order to have a focusing effect, i.e. in order to help push the droplets in the intersection region 64 toward the orifice 20'. The right angle component 150b, which is oppositely directed to the component 52b of trajectory 52', helps push the fine droplets upwardly (as illustrated) toward the orifice 20' and thereby assists with the focusing effect, while at the same time permitting the coarse droplets to continue on a trajectory to impact the inlet plate 18'. The intersection of oppositely directed components of the flows also creates considerable turbulence, which helps to transfer heat to the droplets 50' and to evaporate them rapidly.

Figure 10:
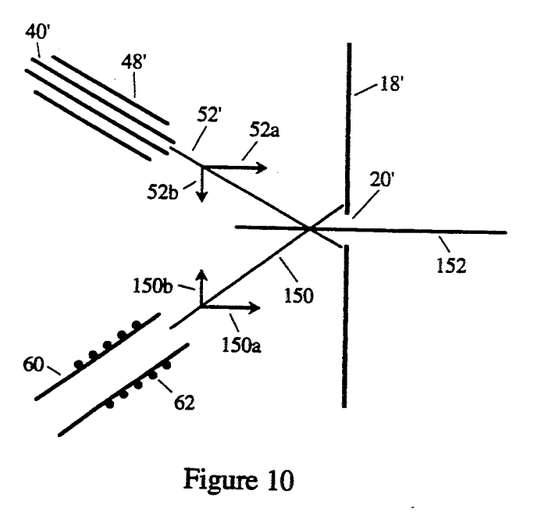
FIG. 10 is a diagrammatic view showing a modification of the FIG. 2 apparatus.

Although the downstream edge of the intersection region 64 is preferably close to but spaced upstream from the orifice 20', e.g. by about 1 centimeter from the orifice, nevertheless improved results are obtained even if the intersection region of the flows borders on or is in the orifice. However intersection bordering or in the orifice 20' tends to force larger droplets through the orifice, creating an increase in background chemical noise, which is generally undesirable.

Figure 13:
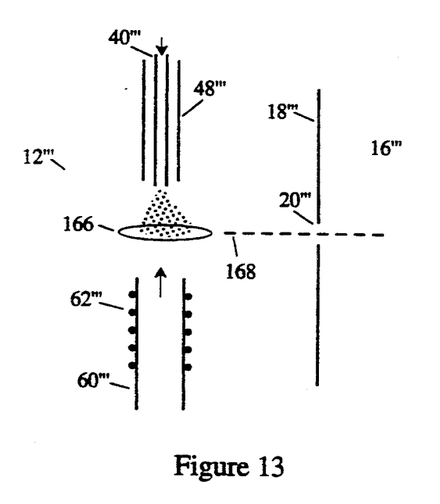
FIG. 13 is a diagrammatic view showing another modification of the FIG. 2 apparatus.
Figure 14:
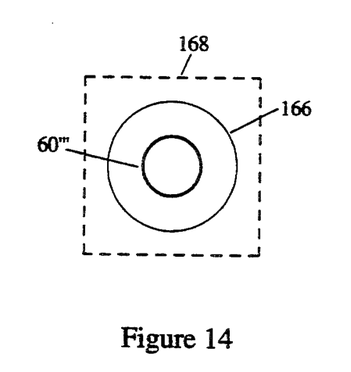
FIG. 14 is a sectional view along an axis of the FIG. 13 apparatus.

The upstream edge of the intersection region 64 preferably does not impinge on tube 40'. It was discovered that it is not desirable to heat the liquid stream directly in the capillary tube of the nebulizer spray device by so directing the heated gas stream at the sprayer tip or heating it by other means such as electrical resistive heating. If tube 40° transferring the liquid is heated directly or indirectly (by passing a hot gas directly over tube 40') it is difficult to avoid momentary overheating of the liquid which leads to boiling and degassing of the liquid in the tube resulting in instabilities in the spray and ion generation process, tube plugging from solids deposition, sensitivity loss, and thermal degradation of compounds. Applying the heat after the liquid and sample leave tube 40' as a spray of droplets represents a distinct advantage of the preferred embodiments of this invention over one that directly heats the liquid in the tube or heats the nebulizer gas surrounding tube 40' and flowing within tube 48'. The heat can now be selectively deposited in the region where it is required, in the droplet plume 64, thereby avoiding problems that arise when the bulk liquid in tube 40' is heated. (Of course if tube 40° were adequately insulated or cooled, then the hot gas could pass over that tube without thermally degrading the sample.) The temperature of the gas from tube 60 may be set within a wide range, as desired. For example it may range between 100° C. and 850° C.

Although FIGS. 2 and 10 show that the flows from the two sets of tubes shown all have a velocity component directed toward orifice 20', such component can be achieved in other ways. For example, and as shown in FIG. 11 where double primed reference numerals indicate parts corresponding to those of FIGS. 1, 2 and 10, tubes 40'', 48'' and 60'' may be coaxial and aimed at each other, with their common axis 160 being at right angles to the axis 152'' through orifice 20''. In such case the velocity and volume of the gas through tube 60'' are typically made about the same as those from tube 48'', so when the two flows intersect in region 64'' (and allowing for the momentum of the liquid flow), there is no net movement along axis 160. In addition, since the diameter of tube 60'' is now smaller because of the higher velocity gas flow through it (its diameter is typically 6 mm), the intersection region 64'' is smaller than region 64, providing increased concentration of ions. Movement of droplets along axis 152'' toward orifice 20'' is provided by a third flow of gas (e.g. Na) from another tube 162, the axis of which extends through the intersection region 64'' and coincides with axis 152''. The gas flow from tube 162 is typically lower velocity than the gas flows through tubes 48'', 60'' since its main purpose is to move droplets toward orifice 20''. If desired, the gas from tube 162 can also be heated, by heater 164.

It is however preferred to use the arrangement of FIG. 2, or a variation thereof, e.g. as shown in FIG. 12, where the careful balance of the three gas flows shown in FIG. 11 is not required. The net velocity component toward the orifice is provided by the angles of tubes 40' and 60'. In FIG. 12 a slow broad laminar flow is provided of clean gas 165 passing through orifices in tube **165*a*. The flow of gas 165 is across a front much wider than that of region 64 and may have a velocity of between 1 and 10 meters per second. This broad slow flow has the advantage of entraining the ionization region 64 in a purified atmosphere and prevents the secondary vortexes produced by the turbulent mixing in region 64** from recirculating contaminated air from the surrounding environment which would lead to an increase in background chemical noise.

However if desired, the arrangement of FIG. 13 can be used, where triple primed reference numerals indicate parts corresponding to those of the previous figures. In FIG. 13 the tubes 48''', 60''' are aimed directly at each other and at right angles to axis 152''', but there is no third tube. In this case, if the momenta of the flows from tubes 40''', 48''' and from tube 60''' are balanced (i.e. made equal and opposite), the products of the intersection of the flows will spread out in a thin disc 166 in a plane of symmetry 168 (FIG. 14). The plane 168 contains the axis 152''' through orifice 20''' and is at right angles to the common axis 150''' of tubes 48''', 60'''.

In the FIG. 13 arrangement, the intersecting flows do not produce net movement of droplets toward the orifice, and in fact since droplets tend to move along radii of disc 166, some tend to move away from the orifice 20'''. However since with sufficient heating the droplets evaporate to produce ions in milliseconds, and since the ions will then be drawn toward the orifice by the applied electric field, reasonably good results can still be obtained without a third jet. In addition, if the gas curtain chamber 14 is removed and, as shown in FIG. 13, the orifice 20''' leads directly into a vacuum chamber 16''', the "inhaling" effect of the orifice will itself produce an effect similar to that of the third jet, producing net movement of droplets toward the orifice. However without a gas curtain, the orifice 20''' is more likely to clog.

Figure 11:
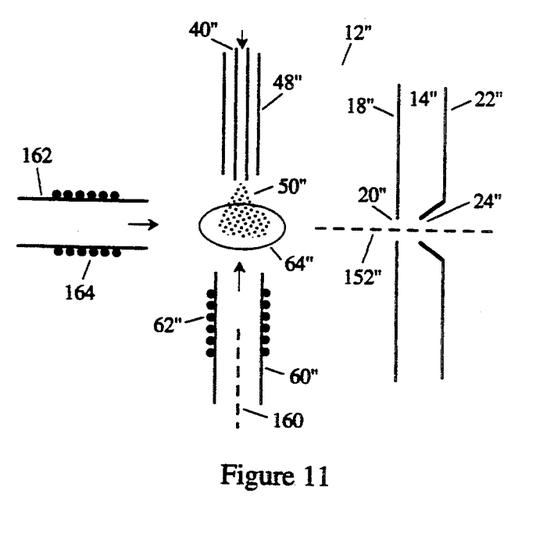
FIG. 11 is a diagrammatic view showing another modification of the FIG. 2 apparatus.
Figure 12:
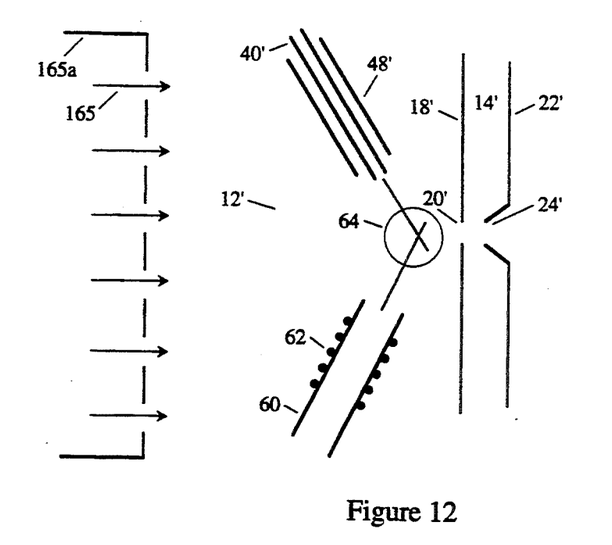
FIG. 12 is a diagrammatic view showing another modification of the FIG. 2 apparatus.

If also desired, the nebulizer gas flow in tube 48 can be reduced to zero (and tube 48 eliminated), and the apparatus can be operated simply as an electrospray source. Any of the arrangements described and shown in FIGS. 2, 11, 12 or 13 may be operated in this manner. The momentum of the respective flows will of course be balanced (e.g. in the FIGS. 11 or 13 arrangement) so that there is no net movement up or down from plane 168. Even at the low liquid flows associated with electrospray, the invention provides a significant improvement in sensitivity, at very low cost.

While preferred embodiments of the invention have been described, it will be realized that changes may be made within the scope of the appended claims.

We claim:

1. A method of analyzing ions from trace sample molecules in a liquid, comprising the steps of:
    (a) providing a chamber having a capillary tube therein, said capillary tube having a free end, said chamber having an orifice member spaced from said free end and having an orifice therein,
    (b) directing said liquid through said capillary tube and out said free end,
    (c) generating an electric field in said chamber between said free end and said orifice member,
    (d) producing from said free end a first flow, of charged droplets of said liquid, and directing said first flow in a first direction,
    (e) producing a second flow, of gas, and heating said second flow,
    (f) directing said second flow in a second direction different from said first direction for said second flow to intersect said first flow at a selected region for turbulent mixing of said first and second flows in said region,
    (g) the heated gas from said second flow acting to assist evaporation of the droplets in said first flow to release ions therefrom,
    (h) and drawing at least some of the ions produced from said droplets through said orifice into an analyzer located outside said chamber beyond said orifice member.

2. The method of claim 1 wherein said selected region is spaced from said free end.

3. The method of claim 2 further including the step of directing a jet of gas past said free end so that said first flow includes said charged droplets and said gas.

4. The method of claim 3 wherein said selected region is within said chamber and spaced from said orifice.

5. The method of claim 4 wherein each of said first and second flows has a component of velocity directed toward said orifice.

6. The method of claim 5 further including the step of providing a third flow of gas, said third flow being directed through said selected region toward said orifice and being a broad laminar flow, to reduce recirculation in said chamber of vortices from said turbulent mixing.

7. The method of claim 4 wherein said first and second flows are directed substantially in opposite directions toward each other.

8. The method of claim 7 further including the step of providing a third flow, of gas, said third flow being directed through said selected region toward said orifice to aid movement of said droplets toward said orifice.

9. The method of claim 8 further including the step of heating said third flow.

10. The method of claim 3 or 4 wherein said gas directed past said free end of said capillary has a velocity in the range 100 to 1000 meters per second and a flow rate in the range 0.25 to 2.0 liters per minute, and said gas of said second flow has a velocity in the range 0.25 to 10 meters per second and a flow rate in the range 0.25 to 10 liters per minute.

11. The method of claim 1 further including the step of providing a gas curtain between said chamber and said analyzer, and flowing gas from said gas curtain through said orifice into said chamber.

12. The method of any of claim 1, 2, 3 or 4 wherein said liquid is directed through said capillary at a flow rate of between 1 microliter and 3,000 microliters per minute.

13. The method of claim 1, 2, 3 or 4 wherein said liquid is directed through said capillary at a rate of between 1 microliter and 2,000 microliters per minute.

14. The method of claim 1, 2, 3 or 4 wherein the temperature of gas in said second flow is between 100° C. and 850° C.

15. The method of any of claims 1 to 5 wherein there is a first axis through said orifice, and wherein said first flow in said first direction is directed along a second axis oriented at an angle to said first axis and ending at a location adjacent but offset slightly from said orifice, to reduce the likelihood of large droplets entering said orifice, and wherein said second flow in said second direction is directed along a second axis, said second axis being at a selected angle to said first and second axes, said selected angle being such that said second flow tends to push fine droplets from said first flow toward said orifice.

16. The method of any of claims 1 to 5 wherein said sample molecules are folded molecules, and further including the step of producing a selected degree of unfolding of said molecules by controlling the temperature of said gas.

17. The method of any of claims 1 to 5 wherein said sample molecules are folded molecules, and further including the step of producing a selected degree of unfolding of said molecules by controlling the temperature of said gas, thereby also increasing the number of electrical charges attached to ions of said molecules emitted from said droplets.

18. In the method of analyzing ions from trace sample molecules in a liquid, said method comprising spraying said liquid in a first direction from an opening to form a plume of electrically charged droplets, the improvement comprising producing a flow of heated gas, and directing said flow in a second direction different from said first direction for said flow to intersect said plume of droplets at a selected region for turbulent mixing of said flow with said droplets in said region, thereby to increase the rate of emission of sample ions from said droplets.

19. The method of claim 18 wherein said selected region is spaced from said opening.

20. The method of claim 18 or 19 wherein said sample molecules are folded molecules, and further including the step of producing a selected degree of unfolding of said molecules by controlling the temperature of said heated gas.

21. The method of claim 18 or 19 wherein said sample molecules are folded molecules, and further including the step of producing a selected degree of unfolding of said molecules in said droplets by controlling the temperature of said heated gas and thereby increasing the number of electrical charges attached to ions of said molecules emitted from said droplets.

22. Apparatus for analyzing ions from trace sample molecules in a liquid comprising:
(a) a chamber,
(b) a capillary tube to receive said liquid and having a first free end in said chamber for discharging said liquid into said chamber,
(c) an orifice member in said chamber having an orifice therein and being spaced from said free end, said orifice defining an outlet from said chamber,
(d) means for creating an electric field between said free end and said orifice member,
(e) means for producing from said free end a first flow, of charged droplets of said liquid, and for directing said first flow in a first direction,
(f) means for producing a second flow of gas in said chamber, and means for heating said second flow,
(g) means for directing said second flow in a second direction different from said first direction for said second flow to intersect said first flow at a selected region for turbulent mixing of said first and second flows at said region,
(h) the heated gas from said second flow acting to assist evaporation of the droplets in said first flow to release ions therefrom,
(i) and means for drawing at least some of the ions produced from said droplets through said orifice into an analyzer located outside said chamber beyond said orifice member.

23. Apparatus according to claim 22 wherein said selected region is spaced from said free end.

24. Apparatus according to claim 22 wherein said selected region is within said chamber and spaced from said orifice.

25. Apparatus according to claim 24 further including means for directing a jet of gas past said free end in said first direction so that said first flow includes said charged droplets and said gas.

26. Apparatus according to claim 25 wherein each of said first and second flows has a component of velocity directed toward said orifice.

27. Apparatus according to claim 26 wherein said first and second flows are directed substantially in opposite directions toward each other.

28. Apparatus according to claim 27 further including means for providing a third flow, of gas, said third flow being directed through said selected region toward said orifice to provide movement of said droplets toward said orifice.

29. Apparatus according to claim 28 further including means for heating said third flow.

30. Apparatus according to claim 22, 23, 24 or 25 further including means interposing a gas curtain between said chamber and said analyzer for flowing gas from said gas curtain to enter said chamber through the orifice.

31. Apparatus according to claim 22, 23, 24 or 25 wherein said heating means for said second flow heats said second flow to between 100° C. and 850° C.

32. In a method of analyzing ions from trace sample molecules in a liquid, said molecules being folded molecules, said method comprising spraying said liquid from an opening to form a plume of electrically charged droplets, each droplet containing said ions, the improvement comprising providing a flow of gas, causing said flow to mix with said plume to aid evaporation of said droplets and emission of ions therefrom, heating said gas to a controlled temperature to cause controlled rapid unfolding of said molecules in said droplets during evaporation of said droplets, and then drawing at least some of the ions emitted from said droplets out of the heated gas and into a vacuum chamber, and analyzing said ions.

33. The method of claim 32 wherein the mixing of said gas with said plume is turbulent mixing.

34. The method of claim 32 or 33 wherein said unfolding occurs within a time period of not greater than about 10 milliseconds.

35. The method of claim 32 or 33 wherein said plume is directed in a first direction and said flow of gas is directed in a second direction different from said first direction and intersects said plume at a location spaced from said opening.

* * * * *